(12) United States Patent
Mylari

(10) Patent No.: US 6,511,981 B2
(45) Date of Patent: *Jan. 28, 2003

(54) COMPOSITIONS AND TREATMENT FOR DIABETIC COMPLICATIONS

(75) Inventor: Banavara L. Mylari, Waterford, CT (US)

(73) Assignee: Pfizer Inc, New York, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 10/003,601

(22) Filed: Oct. 31, 2001

(65) Prior Publication Data

US 2002/0061918 A1 May 23, 2002

Related U.S. Application Data

(62) Division of application No. 09/602,792, filed on Jun. 23, 2000, now Pat. No. 6,413,965.
(60) Provisional application No. 60/141,746, filed on Jun. 30, 1999.

(51) Int. Cl.$^7$ .................... A61K 31/495; A61K 31/395; A61K 31/425; A61K 31/42
(52) U.S. Cl. .................. 514/252.01; 514/210; 514/341; 514/365; 514/367; 514/372; 514/374; 514/378; 514/866
(58) Field of Search ............................ 514/252.01, 365, 514/367, 866, 210, 341, 372, 374, 378

(56) References Cited

U.S. PATENT DOCUMENTS

| 4,939,140 A | | 7/1990 | Larson et al. | |
|---|---|---|---|---|
| 5,990,111 A | * | 11/1999 | Johnson | 514/252 |
| 6,025,353 A | * | 2/2000 | Masferrer et al. | 514/210 |

OTHER PUBLICATIONS

Budavari et al., The Merck Index, 12th Edition, p. 610, abstract No. 3640 (1996).*

* cited by examiner

Primary Examiner—Kevin E. Weddington
(74) Attorney, Agent, or Firm—Peter C. Richardson; Gregg C. Benson; Robert T. Ronau

(57) ABSTRACT

This invention is directed to methods, pharmaceutical compositions and kits comprising an aldose reductase inhibitor (ARI), a prodrug thereof or a pharmaceutically acceptable salt of said ARI or said prodrug and a selective COX-2 inhibitor, a prodrug thereof or a pharmaceutically acceptable salt of said selective COX-2 inhibitor or said prodrug. This invention further relates to methods of using those pharmaceutical compositions for the treatment of diabetic complications such as diabetic neuropathy, diabetic nephropathy, diabetic retinopathy and diabetic cardiomyopathy.

16 Claims, No Drawings

COMPOSITIONS AND TREATMENT FOR DIABETIC COMPLICATIONS

This application is a divisional of U.S. application Ser. No. 09/602,792, filed on Jun. 23, 2000, U.S. Pat No. 6,413,965 entitled Compositions And Treatment For Diabetic Complications, which claims priority from Provisional Application No. 60/141,746, filed Jun. 30, 1999.

BACKGROUND OF THE INVENTION

This invention relates to methods, pharmaceutical compositions and kits comprising an aldose reductase inhibitor (ARI), a prodrug thereof or a pharmaceutically acceptable salt of said ARI or said prodrug and a selective cyclooxygenase-2 (COX-2) inhibitor, a prodrug thereof or a pharmaceutically acceptable salt of said selective COX-2 inhibitor or said prodrug. This invention further relates to methods of using such pharmaceutical compositions for the treatment of diabetic complications such as diabetic neuropathy, diabetic nephropathy, diabetic retinopathy, myocardial infarction, cataracts and diabetic cardiomyopathy.

Aldose reductase inhibitors function by inhibiting the activity of the enzyme aldose reductase, which is primarily responsible for regulating the reduction of aldoses, such as glucose and galactose, to the corresponding polyols, such as sorbitol and galactitol, in humans and other animals. In this way, unwanted accumulations of galactitol in the lens of galactosemic subjects and of sorbitol in the lens, peripheral nervous cord and kidneys of various diabetic subjects are prevented or reduced. Accordingly, aldose reductase inhibitors are of therapeutic value for controlling certain diabetic complications, e.g., diabetic neuropathy, diabetic nephropathy, diabetic cardiomyopathy, myocardial infarction, cataracts and diabetic retinopathy.

Two forms of cylcooxygenase (COX) are known to exist: COX-1 and COX-2, the former being a constitutive form and the latter being an inducible form. COX-1 exists in the stomach, intestines, kidneys and platelets while COX-2 is expressed during inflammation. Both COX enzyme isoforms metabolize arachidonic by a similar mechanism, but each have different substrate specificities. Selective COX-2 inhibitors are advantageous in the treatment of pain and inflammation while avoiding such side effects as gastric and renal toxicity.

SUMMARY OF THE INVENTION

This invention is directed to pharmaceutical compositions comprising an aldose reductase inhibitor (ARI), a prodrug thereof or a pharmaceutically acceptable salt of said ARI or said prodrug; (a) a selective COX-2 inhibitor of formula I,

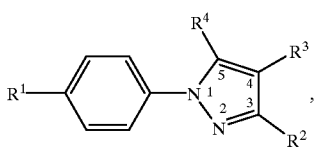

I wherein
$R^1$ is sulfamyl;
$R^2$ is haloalkyl;
$R^3$ is selected from hydrido and alkyl; and
$R^4$ is selected from aryl, cycloalkyl and cycloalkenyl; wherein $R^4$ is optionally substituted at a substitutable position with one or more radicals selected from halo, alkylthio, alkylsulfinyl, alkyl, alkylsulfonyl, cyano, carboxyl, alkoxycarbonyl, amido, N-monoalkylamido, N-monoarylamido, N,N-dialkylamido, N-alkyl-N-arylamido, haloalkyl, hydroxyl, alkoxy, hydroxyalkyl, haloalkoxy, sulfamyl, N-alkylsulfamyl, amino, N-alkylamino, N,N-dialkylamino, heterocyclic, nitro and acylamino;

or a prodrug thereof or a pharmaceutically acceptable salt thereof or of said prodrug;

or (b) a COX-2 inhibitor of formula II,

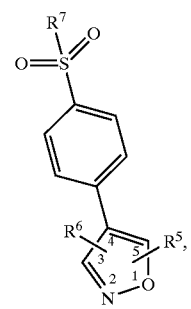

II wherein
$R^5$ is selected from alkyl, carboxyalkyl, alkoxycarbonyl, aminocarbonyl, aminocarbonylalkyl, alkoxycarbonylalkyl, carboxyl, alkoxy, haloalkoxy, aralkoxy, cycloalkylalkoxy, alkylthio, aralkylthio, cycloalkylalkylthio, alkoxyalkyl, aralkoxyalkyl, alkylthioalkyl, aralkylthioalkyl, alkylaminoalkyl, aryloxyalkyl, arylthioalkyl, hydroxyl, amino, hydroxyalkyl, haloalkyl, cycloalkyl, cycloalkylalkyl, aralkyl, halo, alkylamino, aralkylamino, N-alkyl-N-aralkylamino, N-alkyl-N-cycloalkylalkylamino, arylcarbonyloxyalkyl, arylcarbonylthio, alkoxycarbonyloxyalkyl, alkylaminocarbonyloxyalkyl, alkoxycarbonylthioalkyl and alkylaminocarbonylthioalkyl;

$R^6$ is selected from cycloalkyl, cycloalkenyl and aryl; wherein $R^6$ is optionally substituted at a substitutable position with one or more radicals independently selected from alkyl, cyano, carboxyl, alkoxycarbonyl, haloalkyl, hydroxyl, hydroxyalkyl, haloalkoxy, amino, alkylamino, arylamino, aminoalkyl, nitro, alkoxyalkyl, alkylsulfinyl, alkylsulfonyl, aminosulfonyl, halo, alkoxy and alkylthio; and $R^7$ is selected from lower alkyl, hydroxyl and amino; a prodrug thereof or a pharmaceutically acceptable salt thereof or of said prodrug;

and a pharmaceutically acceptable carrier, vehicle or diluent.

This invention is also directed to methods of treating a diabetic complication in a mammal comprising administering to said mammal a pharmaceutical composition as set forth hereinabove. In particular, such diabetic complications as, for example, diabetic neuropathy, diabetic nephropathy, diabetic cardiomyopathy, myocardial infarction, cataracts and diabetic retinopathy can be treated by the methods of this invention.

This invention is also directed to kits comprising:

a) a first unit dosage form comprising an aldose reductase inhibitor (ARI), a prodrug thereof or a pharmaceuti cally acceptable salt of said ARI or said prodrug and a pharmaceutically acceptable carrier, vehicle or diluent;

b) A second unit dosage form comprising a selective COX-2 inhibitor of formula I,

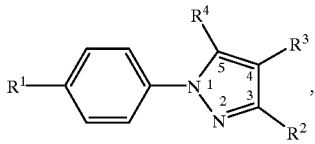

wherein
$R^1$ is sulfamyl;
$R^2$ is haloalkyl;
$R^3$ is selected from hydrido and alkyl; and
$R^4$ is selected from aryl, cycloalkyl and cycloalkenyl; wherein $R^4$ is optionally substituted at a substitutable position with one or more radicals selected from halo, alkylthio, alkylsulfinyl, alkyl, alkylsulfonyl, cyano, carboxyl, alkoxycarbonyl, amido, N-monoalkylamido, N-monoarylamido, N,N-dialkylamido, N-alkyl-N-arylamido, haloalkyl, hydroxyl, alkoxy, hydroxyalkyl, haloalkoxy, sulfamyl, N-alkylsulfamyl, amino, N-alkylamino, N,N-dialkylamino, heterocyclic, nitro and acylamino;

a prodrug thereof or a pharmaceutically acceptable salt of said compound or said prodrug; or a COX-2 inhibitor of formula II,

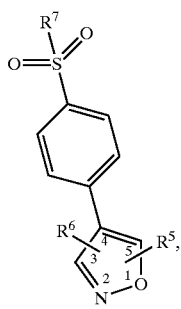

wherein
$R^5$ is selected from alkyl, carboxyalkyl, alkoxycarbonyl, aminocarbonyl, aminocarbonylalkyl, alkoxycarbonylalkyl, carboxyl, alkoxy, haloalkoxy, aralkoxy, cycloalkylalkoxy, alkylthio, aralkylthio, cycloalkylalkylthio, alkoxyalkyl, aralkoxyalkyl, alkylthioalkyl, aralkylthioalkyl, alkylaminoalkyl, aryloxyalkyl, arylthioalkyl, hydroxyl, amino, hydroxyalkyl, haloalkyl, cycloalkyl, cycloalkylalkyl, aralkyl, halo, alkylamino, aralkylamino, N-alkyl-N-aralkylamino, N-alkyl-N-cycloalkylalkylamino, arylcarbonyloxyalkyl, arylcarbonylthio, alkoxycarbonyloxyalkyl, alkylaminocarbonyloxyalkyl, alkoxycarbonylthioalkyl and alkylaminocarbonylthioalkyl;
$R^6$ is selected from cycloalkyl, cycloalkenyl and aryl; wherein $R^6$ is optionally substituted at a substitutable position with one or more radicals independently selected from alkyl, cyano, carboxyl, alkoxycarbonyl, haloalkyl, hydroxyl, hydroxyalkyl, haloalkoxy, amino, alkylamino, arylamino, aminoalkyl, nitro, alkoxyalkyl, alkylsulfinyl, alkylsulfonyl, aminosulfonyl, halo, alkoxy and alkylthio; and $R^7$ is selected from lower alkyl, hydroxyl and amino; a prodrug thereof or a pharmaceutically acceptable salt of said compound or said prodrug; and c) a container.

This invention is also directed to methods of treating a diabetic complication in a mammal comprising administering to said mammal an ARI, a prodrug thereof or a pharmaceutically acceptable salt of said ARI or said prodrug; and (a) a selective COX-2 inhibitor of formula I

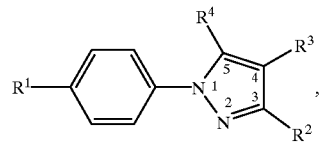

wherein
$R^1$ is sulfamyl;
$R^2$ is haloalkyl;
$R^3$ is selected from hydrido and alkyl; and
$R^4$ is selected from aryl, cycloalkyl and cycloalkenyl; wherein $R^4$ is optionally substituted at a substitutable position with one or more radicals selected from halo, alkylthio, alkylsulfinyl, alkyl, alkylsulfonyl, cyano, carboxyl, alkoxycarbonyl, amido, N-monoalkylamido, N-monoarylamido, N,N-dialkylamido, N-alkyl-N-arylamido, haloalkyl, hydroxyl, alkoxy, hydroxyalkyl, haloalkoxy, sulfamyl, N-alkylsulfamyl, amino, N-alkylamino, N,N-dialkylamino, heterocyclic, nitro and acylamino;

a prodrug thereof or a pharmaceutically acceptable salt of said compound or said prodrug; or (b) a COX-2 inhibitor of formula II,

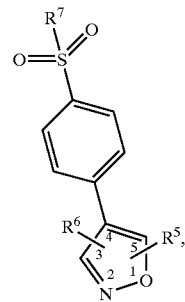

wherein
$R^5$ is selected from alkyl, carboxyalkyl, alkoxycarbonyl, aminocarbonyl, aminocarbonylalkyl, alkoxycarbonylalkyl, carboxyl, alkoxy, haloalkoxy, aralkoxy, cycloalkylalkoxy, alkylthio, aralkylthio, cycloalkylalkylthio, alkoxyalkyl, aralkoxyalkyl, alkylthioalkyl, aralkylthioalkyl, alkylaminoalkyl, aryloxyalkyl, arylthioalkyl, hydroxyl, amino, hydroxyalkyl, haloalkyl, cycloalkyl, cycloalkylalkyl, aralkyl, halo, alkylamino, aralkylamino, N-alkyl-N-aralkylamino, N-alkyl-N-cycloalkylalkylamino, arylcarbonyloxyalkyl, arylcarbonylthio, alkoxycarbonyloxyalkyl, alkylaminocarbonyloxyalkyl, alkoxycarbonylthioalkyl and alkylaminocarbonylthioalkyl;
$R^6$ is selected from cycloalkyl, cycloalkenyl and aryl; wherein $R^6$ is optionally substituted at a substitutable position with one or more radicals independently selected from alkyl, cyano, carboxyl, alkoxycarbonyl, haloalkyl, hydroxyl, hydroxyalkyl, haloalkoxy, amino, alkylamino, arylamino, aminoalkyl, nitro, alkoxyalkyl, alkylsulfinyl, alkylsulfonyl, aminosulfonyl, halo, alkoxy and alkylthio; and $R^7$ is selected from lower alkyl, hydroxyl and amino;

a prodrug thereof or a pharmaceutically acceptable salt of said compound or said prodrug.

It is preferred that the ARI and the selective COX-2 inhibitor are administered together.

It is also preferred that the ARI and the COX-2 inhibitor are administered separately in any order.

In the compositions, methods and kits of this invention, it is preferred that said ARI is fidarestat, epalrestat, minalrestat, SPR-210, zenarastat or zopolrestat, a prodrug of thereof or a pharmaceutically acceptable salt of said ARI or of said prodrug. It is especially preferred that said ARI is zopolrestat, a prodrug thereof or a pharmaceutically acceptable salt of zopolrestat or of said prodrug and said COX-2 inhibitor is celecoxib or valdecoxib, a prodrug thereof or a pharmaceutically acceptable salt of said selective COX-2 inhibitor or of said prodrug.

Where used herein and in the appendant claims, the phrase "lower alkyl" refers to alkyl groups containing one to four carbon atoms straight chain or branched.

DETAILED DESCRIPTION OF THE INVENTION

The COX-2 inhibitors of formula I, including celecoxib, which are used in the compositions, methods and kits of this invention are prepared according to methods reported in U.S. Pat. No. 5,466,823, which is hereby wholly incorporated herein by reference. Celecoxib is also known as benzenesulfonamide, 4-[5-(4-methylphenyl)-3-(trifluoromethyl)-1H-pyrazol-1-yl]- and has the following chemical structure:

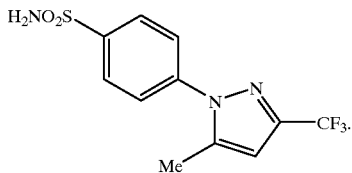

The COX-2 inhibitors of formula II, including valdecoxib, which are used in the compositions, methods and kits of this invention are prepared according to methods reported in U.S. Pat. No. 5,633,272, which is hereby wholly incorporated herein by reference. Valdecoxib is also known as benzenesulfonamide, 4-(5-methyl-3-phenyl-4-isoxazolyl)- and has the following chemical structure:

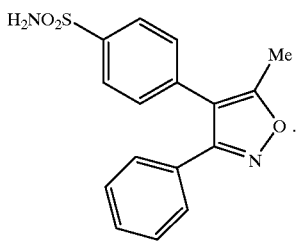

The methods, compositions and kits of this invention are useful in treating diabetic complications, including, but not limited to, diabetic neuropathy, diabetic nephropathy, diabetic cardiomyopathy, myocardial infarction, cataracts and diabetic retinopathy.

The term "treating", as used herein, refers to retarding, arresting or reversing the progress of, or alleviating or preventing either the disorder or condition to which the term "treating" applies, or one or more symptoms of such disorder or condition. The term "treatment", as used herein, refers to the act of treating a disorder, symptom or condition, as the term "treating" is defined above.

Any aldose reductase inhibitor may be used in the pharmaceutical. Any aldose reductast inhibitor may be used in the pharmaceutical compositions, methods and kits of this invention. The term aldose reductase inhibitor refers to a compound which inhibits the bioconversion of glucose to sorbitol catalyzed by the enzyme aldose reductase. Such inhibition is readily determined by those skilled in the art according to standard assays (J. Malone, *Diabetes*, 29:861–864, 1980. "Red Cell Sorbitol, an Indicator of Diabetic Control"). The following patents and patent applications, each of which is hereby wholly incorporated herein by reference, exemplify aldose reductase inhibitors which can be used in the compositions, methods and kits of this invention, and refer to methods of preparing those aldose reductase inhibitors: U.S. Pat. Nos. 4,251,528; 4,600,724; 4,464,382; 4,791,126; 4,831,045; 4,734,419; 4,883,800; 4,883,410; 4,883,410; 4,771,050; 5,252,572; 5,270,342; 5,430,060; 4,130,714; 4,540,704; 4,438,272; 4,436,745, 4,438,272; 4,436,745; 4,438,272; 4,436,745; 4,438,272; 4,980,357; 5,066,659; 5,447,946; 5,037,831.

A variety of aldose reductase inhibitors are specifically described and referenced below, however, other aldose reductase inhibitors will be known to those skilled in the art. Also, common chemical USAN names or other designations are in parentheses where applicable, together with reference to appropriate patent literature disclosing the compound.

Accordingly, examples of aldose reductase inhibitors useful in the compositions and methods of this invention include:

1. 3-(4-bromo-2-fluorobenzyl)-3,4-dihydro-4-oxo-1-phthalazineacetic acid (ponalrestat, U.S. Pat. No. 4,251,528);

2. N[[(5-trifluoromethyl)-6-methoxy-1-naphthalenyl]thioxomethyl}-N-methylglycine (tolrestat, U.S. Pat. No. 4,600,724);

3. 5-[(Z,E)-β-methylcinnamylidene]-4-oxo-2-thioxo-3-thiazolideneacetic acid (epalrestat, U.S. Pat. Nos. 4,464,382, 4,791,126, 4,831,045);

4. 3-(4-bromo-2-fluorobenzyl)-7-chloro-3,4-dihydro-2,4-dioxo-1(2H)-quinazolineacetic acid (zenarestat, U.S. Pat. Nos. 4,734,419, and 4,883,800);

5. 2R,4R-6,7-dichloro-4-hydroxy-2-methylchroman-4-acetic acid (U.S. Pat. No. 4,883,410);

6. 2R,4R-6,7-dichloro-6-fluoro-4-hydroxy-2-methylchroman-4-acetic acid (U.S. Pat. No. 4,883,410);

7. 3,4-dihydro-2,8-diisopropyl-3-oxo-2H-1,4-benzoxazine-4-acetic acid (U.S. Pat. No. 4,771,050);

8. 3,4-dihydro-3-oxo-4-[(4,5,7-trifluoro-2-benzothiazolyl)methyl]-2H-1,4-benzothiazine-2-acetic acid (SPR-210, U.S. Pat. No. 5,252,572);

9. N-[3,5-dimethyl-4-[(nitromethyl)sulfonyl]phenyl]-2-methyl-benzeneacetamide (ZD5522, U.S. Pat. Nos. 5,270,342 and 5,430,060);

10. (S)-6-fluorospiro[chroman-4,4'-imidazolidine]-2,5'-dione (sorbinil, U.S. Pat. No. 4,130,714);

11. d-2-methyl-6-fluoro-spiro(chroman-4',4'-imidazolidine)-2',5'-dione (U.S. Pat. No. 4,540,704);

12. 2-fluoro-spiro(9H-fluorene-9,4'-imidazolidine)-2',5'-dione (U.S. Pat. No. 4,438,272);

13. 2,7-di-fluoro-spiro(9H-fluorene-9,4'-imidazolidine)-2',5'-dione (U.S. Pat. Nos. 4,436,745, 4,438,272);

14. 2,7-di-fluoro-5-methoxy-spiro(9H-fluorene-9,4'-imidazolidine)-2',5'-dione (U.S. Pat. Nos. 4,436,745, 4,438,272);

15. 7-fluoro-spiro(5H-indenol[1,2-b]pyridine-5,3'-pyrrolidine)-2,5'-dione (U.S. Pat. Nos. 4,436,745, 4,438,272);

16. d-cis-6'-chloro-2',3'-dihydro-2'-methyl-spiro-(imidazolidine-4,4'-4'H-pyrano(2,3-b)pyridine)-2,5-dione (U.S. Pat. No. 4,980,357);

17. spiro[imidazolidine-4,5'(6H)-quinoline]-2,5-dione-3'-chloro-7',8'-dihydro-7'-methyl-(5'-cis) (U.S. Pat. No. 5,066,659);

18. (2S,4S)-6-fluoro-2',5'-dioxospiro(chroman-4,4'-imidazolidine)-2-carboxamide (fidarestat, U.S. Pat. No. 5,447,946); and 19. 2-[(4-bromo-2-fluorophenyl)methyl]-6-fluorospiro[isoquinoline-4(1 H),3'-pyrrolidine]-1,2', 3,5'(2H)-tetrone (minalrestat, U.S. Pat. No. 5,037,831).

All of the foregoing patents disclosing ARI compounds are wholly incorporated herein by reference.

Other aldose reductase inhibitors include compounds of formula A,

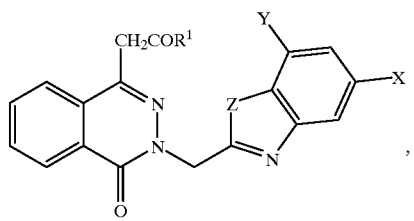

and pharmaceutically acceptable salts thereof, wherein

Z in the compound of formula A is O or S;

$R^1$ in the compound of formula A is hydroxy or a group capable of being removed in vivo to produce a compound of formula A wherein $R^1$ is OH; and X and Y in the compound of formula A are the same or different and are selected from hydrogen, trifluoromethyl, fluoro, and chloro.

A preferred subgroup within the above group of aldose reductase inhibitors includes numbered compounds 1, 2, 3, 4, 5, 6, 9, 10, and 17, and the following compounds of formula A:

20. 3,4-dihydro-3-(5-fluorobenzothiazol-2-ylmethyl)-4-oxophthalazin-1-yl-acetic acid [$R^1$=hydroxy; X=F; Y=H];

21. 3-(5,7-difluorobenzothiazol-2-ylmethyl)-3,4-dihydro-4-oxophthalazin-1-ylacetic acid [$R^1$=hydroxy; X=Y=F];

22. 3-(5-chlorobenzothiazol-2-ylmethyl)-3,4-dihydro-4-oxophthalazin-1-ylacetic acid [$R^1$=hydroxy; X=Cl; Y=H];

23. 3-(5,7-dichlorobenzothiazol-2-ylmethyl)-3,4-dihydro-4-oxophthalazin-1-ylacetic acid [$R^1$=hydroxy; X=Y=Cl];

24. 3,4-dihydro-4-oxo-3-(5-trifluoromethylbenzoxazol-2-ylmethyl)phthalazin-1-ylacetic acid [$R^1$=hydroxy; X=$CF_3$; Y=H];

25. 3,4-dihydro-3-(5-fluorobenzoxazol-2-ylmethyl)-4-oxophthalazin-1-yl-acetic acid [$R^1$=hydroxy; X=F; Y=H];

26. 3-(5,7-difluorobenzoxazol-2-ylmethyl)-3,4-dihydro-4-oxophthalazin-1-ylacetic acid [$R^1$=hydroxy; X=Y=F];

27. 3-(5-chlorobenzoxazol-2-ylmethyl)-3,4-dihydro-4-oxophthalazin-1-ylacetic acid [$R^1$=hydroxy; X=Cl; Y=H];

28. 3-(5,7-dichlorobenzoxazol-2-ylmethyl)-3,4-dihydro-4-oxophthalazin-1-ylacetic acid [$R^1$=hydroxy; X=Y=Cl]; and 29. zopolrestat; 1-phthalazineacetic acid, 3,4-dihydro-4-oxo-3-[[5-(trifluoromethyl)-2-benzothiazolyl]methyl]-[$R^1$=hydroxy; X=trifluoromethyl; Y=H].

In compounds 20–23 and 29, Z is S. In compounds 24–28, Z is O.

Of the above subgroup, compounds 20–29 are more preferred with compound 29 especially preferred.

Said compounds of formula A are prepared as disclosed in U.S. Pat. No. 4,939,140, which is wholly incorporated herein by reference.

The aldose reductase inhibitor compounds of this invention are readily available or can be easily synthesized by those skilled in the art using conventional methods of organic synthesis, particularly in view of the pertinent patent specifications.

The activity of the selective COX-2 inhibitors of the present invention may be demonstrated by the following assays. COX-1 activity is determined by methods well known to those skilled in the art. The human cell based COX-2 assay is carried out as previously described (Moore et al., *Inflam. Res.*, 45, 54, 1996). The in vivo Carrageenan induced foot edema rat study is carried out as previously described in Winter et al., *Proc. Soc. Exp. Biol. Med.*, 111, 544, 1962.

COX-2 selectivity can be determined by methods well known to those skilled in the art and particularly by ratio in terms of $IC_{50}$ value of COX-1 inhibition to COX-2 inhibition. In general, it can be said that a compound showing a COX-1/COX-2 inhibition ratio of more than 2 has good COX-2 selectivity.

This invention relates both to methods of treating diabetic complications in which the ARI, prodrug thereof or pharmaceutically acceptable salt of said ARI or said prodrug and said selective COX-2 inhibitor, prodrug thereof or pharmaceutically acceptable salt of said selective COX-2 inhibitor or said prodrug are administered together, as part of the same pharmaceutical composition, and to methods in which these two active agents are administered separately, as part of an appropriate dosage regimen designed to obtain the benefits of the combination therapy. The appropriate dosage regimen, the amount of each dose administered and the intervals between doses of the active agents will depend upon the ARI and the selective COX-2 inhibitor being used, the type of pharmaceutical formulations being used, the characteristics of the subject being treated and the severity of the complications. Generally, in carrying out the methods of this invention, an effective dosage for the aldose reductase inhibitors of this invention is in the range of about 0.01 mg/kg/day to 100 mg/kg/day in single or divided doses, preferably 0.1 mg/kg/day to 20 mg/kg/day in single or divided doses and the selective COX-2 inhibitor will be administered in single or divided doses. Selective COX-2 inhibitors will generally be administered in amounts ranging from about 0.01 mg/kg/day in single or divided doses, preferably 10 mg to about 300 mg per day for an average subject, depending upon the selective COX-2 inhibitor and the route of administration. However, some variation in dosage will necessarily occur depending on the condition of the subject being treated. The person responsible for administration will, in any event, determine the appropriate dose for the individual subject.

Administration of the pharmaceutical compositions of this invention can be via any method which delivers a composition of this invention preferentially to the desired tissue (e.g., nerve, kidney, retina and/or cardiac tissues). These methods include oral routes, parenteral, intraduodenal routes, etc. Generally, the compositions of the present invention are administered in single (e.g., once daily) or multiple doses or via constant infusion.

Pharmaceutical compositions comprising an aldose reductase inhibitor, a prodrug thereof or a pharmaceutically acceptable salt of said aldose reductase inhibitor or said prodrug and a selective COX-2 inhibitor, a prodrug thereof or a pharmaceutically acceptable salt of said selective COX-2 inhibitor or said prodrug are hereinafter referred to, collectively, as "the active compositions of this invention."

The active compositions of this invention may be administered to a subject in need of treatment by a variety of conventional routes of administration, including orally, topically, parenterally, e.g., intravenously, subcutaneously or intramedullary. Further, the active compositions of this invention may be administered intranasally, as a rectal suppository or using a "flash" formulation, i.e., allowing the medication to dissolve in the mouth without the need to use water.

The active compositions of this invention may be administered alone or in combination with pharmaceutically acceptable carriers, vehicles or diluents, in either single or multiple doses. Suitable pharmaceutical carriers, vehicles and diluents include inert solid diluents or fillers, sterile aqueous solutions and various organic solvents. The pharmaceutical compositions formed by combining the active compositions of this invention and the pharmaceutically acceptable carriers, vehicles or diluents are then readily administered in a variety of dosage forms such as tablets, powders, lozenges, syrups, injectable solutions and the like. These pharmaceutical compositions can, if desired, contain additional ingredients such as flavorings, binders, excipients and the like. Thus, for purposes of oral administration, tablets containing various excipients such as sodium citrate, calcium carbonate and calcium phosphate may be employed along with various disintegrants such as starch, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tabletting purposes. Solid compositions of a similar type may also be employed as fillers in soft and hard filled gelatin capsules. Preferred materials for this include lactose or milk sugar and high molecular weight polyethylene glycols. When aqueous suspensions or elixirs are desired for oral administration, the essential active ingredient therein may be combined with various sweetening or flavoring agents, coloring matter or dyes and, if desired, emulsifying or suspending agents, together with diluents such as water, ethanol, propylene glycol, glycerin and combinations thereof.

For parenteral administration, solutions of the active compositions of this invention in sesame or peanut oil, aqueous propylene glycol, or in sterile aqueous solutions may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, the sterile aqueous media employed are all readily available by standard techniques known to those skilled in the art.

Generally, a composition of this invention is administered orally, or parenterally (e.g., intravenous, intramuscular, subcutaneous or intramedullary). Topical administration may also be indicated, for example, where the patient is suffering from gastrointestinal disorders or whenever the medication is best applied to the surface of a tissue or organ as determined by the attending physician.

For buccal administration the composition (two active agents administered together or separately) may take the form of tablets or lozenges formulated in a conventional manner.

For intranasal administration or administration by inhalation, the active compounds of the invention (two active agents administered together or separately) are conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch.

For purposes of transdermal (e.g.,topical) administration, dilute sterile, aqueous or partially aqueous solutions (usually in about 0.1% to 5% concentration), otherwise similar to the above parenteral solutions, are prepared.

Methods of preparing various pharmaceutical compositions with a certain amount of active ingredient are known, or will be apparent in light of this disclosure, to those skilled in this art. For examples of methods of preparing pharmaceutical compositions, see *Remington's Pharmaceutical Sciences,* Mack Publishing Company, Easton, Pa., 19th Edition (1995).

The active compositions of this invention contain an amount of both an aldose reductase inhibitor, a prodrug thereof or a pharmaceutically acceptable salt of said aldose reductase inhibitor or said prodrug and a selective COX-2 inhibitor, a prodrug thereof or a pharmaceutically acceptable salt of said selective COX-2 inhibitor or said prodrug. The amount of each of those ingredients may independently be, for example, 0.0001%–95% of the total amount of the composition, where the total amount of each may not, of course, exceed 100%. In any event, the composition or formulation to be administered will contain a quantity of each of the components of the composition according to the invention in an amount effective to treat the disease/condition of the subject being treated.

Since the present invention has an aspect that relates to the treatment of the disease/conditions described herein with a combination of active ingredients which may be administered separately, the invention also relates to combining separate pharmaceutical compositions in kit form. The kit comprises two separate pharmaceutical compositions: an aldose reductase inhibitor, a prodrug thereof or a salt of such aldose reductase inhibitor or prodrug and a selective COX-2 inhibitor, a prodrug thereof or a salt of said selective COX-2 inhibitor or prodrug as described above. The kit comprises a container for containing the separate compositions such as a divided bottle or a divided foil packet. Typically the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc . . . Second Week, Monday, Tuesday, . . . " etc. Other variations of memory aids will be readily apparent. A "daily dose" can be a single tablet or capsule or several pills or capsules to be taken on a given day. Also, a daily dose of the aldose reductase inhibitor can consist of one tablet or capsule while a daily dose of the COX-2 inhibitor can consist of several tablets or capsules and vice versa. The memory aid should reflect this.

In another specific embodiment of the invention, a dispenser designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

The compositions of this invention generally will be administered in a convenient formulation. The following formulation examples are illustrative only and are not intended to limit the scope of the present invention.

In the formulations which follow, "active ingredient" means a combination of the compounds of this invention.

Formulation 1: Gelatin Capsules
Hard gelatin capsules are prepared using the following:

| Ingredient | Quantity (mg/capsule) |
|---|---|
| Active ingredient | 0.25–100 |
| Starch, NF | 0–650 |
| Starch flowable powder | 0–50 |
| Silicone fluid 350 centistokes | 0–15 |

A tablet formulation is prepared using the ingredients below:

Formulation 2: Tablets

| Ingredient | Quantity (mg/tablet) |
|---|---|
| Active ingredient | 0.25–100 |
| Cellulose, microcrystalline | 200–650 |
| Silicon dioxide, fumed | 10–650 |
| Stearate acid | 5–15 |

The components are blended and compressed to form tablets.

Alternatively, tablets each containing 0.25–100 mg of active ingredients are made up as follows:

Formulation 3: Tablets

| Ingredient | Quantity (mg/tablet) |
|---|---|
| Active ingredient | 0.25–100 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.25–100 mg of active ingredient per 5 ml dose are made as follows:

Formulation 4: Suspensions

| Ingredient | Quantity (mg/5 ml) |
|---|---|
| Active ingredient | 0.25–100 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified Water to | 5 mL |

The active ingredient is passed through a No. 45 mesh U.S. sieve and mixed with the sodium carboxymethyl cellulose and syrup to form smooth paste. The benzoic acid solution, flavor, and color are diluted with some of the water and added, with stirring. Sufficient water is then added to produce the required volume. An aerosol solution is prepared containing the following ingredients:

| Formulation 5: Aerosol | |
|---|---|
| Ingredient | Quantity (% by weight) |
| Active ingredient | 0.25 |
| Ethanol | 25.75 |
| Propellant 22 (chlorodifluoromethane) | 74.00 |

The active ingredient is mixed with ethanol and the mixture added to a portion of the propellant 22, cooled to 30° C., and transferred to a filling device. The required amount is then fed to a stainless steel container and diluted with the remaining propellant. The valve units are then fitted to the container. Suppositories are prepared as follows:

| Formulation 6: Suppositories | |
|---|---|
| Ingredient | Quantity (mg/suppository) |
| Active ingredient | 250 |
| Saturated fatty acid glycerides | 2,000 |

The active ingredient is passed through a No. 60 mesh U.S. sieve and suspended in the saturated fatty acid glycerides previously melted using the minimal necessary heat. The mixture is then poured into a suppository mold of nominal 2 g capacity and allowed to cool.

An intravenous formulation is prepared as follows:

| Formulation 7: Intravenous Solution | |
|---|---|
| Ingredient | Quantity |
| Active ingredient | 25 mg–10,000 mg |
| Isotonic saline | 1,000 mL |

The solution of the above ingredients is intravenously administered to a patient.

What is claimed is:

1. A pharmaceutical composition comprising an aldose reductase inhibitor (ARI), a prodrug thereof or a pharmaceutically acceptable salt of said ARI or said prodrug; a selective COX-2 inhibitor of formula II,

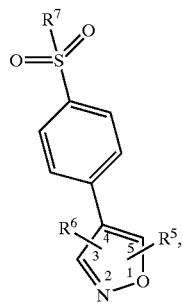

II wherein $R^5$ is selected from alkyl, carboxyalkyl, alkoxycarbonyl, aminocarbonyl, aminocarbonylalkyl, alkoxycarbonylalkyl, carboxyl, alkoxy, haloalkoxy, aralkoxy, cycloalkylalkoxy, alkylthio, aralkylthio, cycloalkylalkylthio, alkoxyalkyl, aralkoxyalkyl, alkylthioalkyl, aralkylthioalkyl, alkylaminoalkyl, aryloxyalkyl, arylthioalkyl, hydroxyl, amino, hydroxyalkyl, haloalkyl, cycloalkyl, cycloalkylalkyl, aralkyl, halo, alkylamino, aralkylamino, N-alkyl-N-aralkylamino, N-alkyl-N-cycloalkylalkylamino, arylcarbonyloxyalkyl, arylcarbonylthio, alkoxycarbonyloxyalkyl, alkylaminocarbonyloxyalkyl, alkoxycarbonylthioalkyl and alkylaminocarbonylthioalkyl;

$R^6$ is selected from cycloalkyl, cycloalkenyl and aryl; wherein $R^6$ is optionally substituted at a substitutable position with one or more radicals independently selected from alkyl, cyano, carboxyl, alkoxycarbonyl, haloalkyl, hydroxyl, hydroxyalkyl, haloalkoxy, amino, alkylamino, arylamino, aminoalkyl, nitro, alkoxyalkyl, alkylsulfinyl, alkylsulfonyl, aminosulfonyl, halo, alkoxy and alkylthio; and $R^7$ is selected from lower alkyl, hydroxyl and amino; a prodrug thereof or a pharmaceutically acceptable salt of said selective COX-2 inhibitor of formula II or of said prodrug; and a pharmaceutically acceptable carrier, vehicle or diluent.

2. A composition of claim 1 wherein said selective COX-2 inhibitor is valdecoxib, a prodrug thereof or a pharmaceutically acceptable salt of valdecoxib or said prodrug.

3. A composition of claim 1 wherein said ARI is fidarestat, epalrestat, minalrestat, SPR-210, zenarastat or zopolrestat, a prodrug of said compound or a pharmaceutically acceptable salt of said ARI or said prodrug.

4. A composition of claim 1 wherein said ARI is zopolrestat, a prodrug thereof or a pharmaceutically acceptable salt of zopolrestat or said prodrug.

5. A composition of claim 3 wherein said selective COX-2 inhibitor is valdecoxib, a prodrug thereof or a pharmaceutically acceptable salt of valdecoxib or said prodrug.

6. A composition of claim 4 wherein said selective COX-2 inhibitor is valdecoxib, a prodrug thereof or a pharmaceutically acceptable salt of valdecoxib or said prodrug.

7. A method of treating a mammal suffering from a diabetic complication comprising administering to said mammal a pharmaceutical composition of claim 1.

8. A method of claim 7 wherein said diabetic complication is diabetic neuropathy, diabetic nephropathy, diabetic cardiomyopathy, diabetic retinopathy, cataracts or myocardial infarction.

9. A method of treating a mammal suffering from a diabetic complication comprising administering to said mammal a pharmaceutical composition of claim 2.

10. A kit comprising:

a) a first unit dosage form comprising an aldose reductase inhibitor (ARI), a prodrug thereof or a pharmaceutically acceptable salt of said ARI or said prodrug and a pharmaceutically acceptable carrier, vehicle or diluent;

b) a second unit dosage form comprising a selective COX-2 inhibitor of formula II,

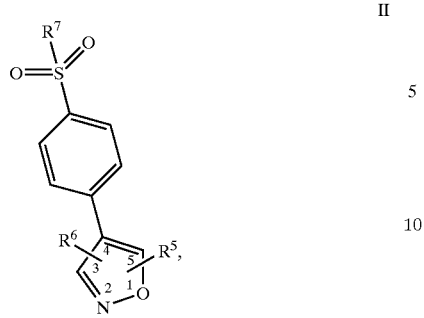
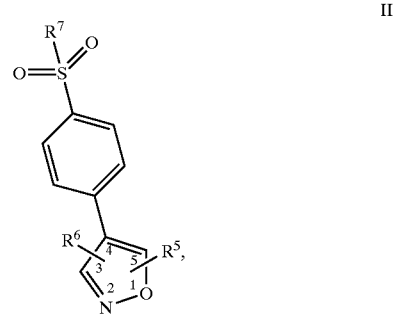

wherein

R⁵ is selected from alkyl, carboxyalkyl, alkoxycarbonyl, aminocarbonyl, aminocarbonylalkyl, alkoxycarbonylalkyl, carboxyl, alkoxy, haloalkoxy, aralkoxy, cycloalkylalkoxy, alkylthio, aralkylthio, cycloalkylalkylthio, alkoxyalkyl, aralkoxyalkyl, alkylthioalkyl, aralkylthioalkyl, alkylaminoalkyl, aryloxyalkyl, arylthioalkyl, hydroxyl, amino, hydroxyalkyl, haloalkyl, cycloalkyl, cycloalkylalkyl, aralkyl, halo, alkylamino, aralkylamino, N-alkyl-N-aralkylamino, N-alkyl-N-cycloalkylalkylamino, arylcarbonyloxyalkyl, arylcarbonylthio, alkoxycarbonyloxyalkyl, alkylaminocarbonyloxyalkyl, alkoxycarbonylthioalkyl and alkylaminocarbonylthioalkyl;

R⁶ is selected from cycloalkyl, cycloalkenyl and aryl; wherein R⁶ is optionally substituted at a substitutable position with one or more radicals independently selected from alkyl, cyano, carboxyl, alkoxycarbonyl, haloalkyl, hydroxyl, hydroxyalkyl, haloalkoxy, amino, alkylamino, arylamino, aminoalkyl, nitro, alkoxyalkyl, alkylsulfinyl, alkylsulfonyl, aminosulfonyl, halo, alkoxy and alkylthio; and R⁷ is selected from lower alkyl, hydroxyl and amino;

a prodrug thereof or a pharmaceutically acceptable salt of said selective COX-2 inhibitor of formula II or said prodrug; and c) a container.

11. A method of treating a diabetic complication in a mammal comprising administering to said mammal an ARI, a prodrug thereof or a pharmaceutically acceptable salt of said ARI or said prodrug; and a selective COX-2 inhibitor of formula II, wherein R⁵ is selected from alkyl, carboxyalkyl, alkoxycarbonyl, aminocarbonyl, aminocarbonylalkyl, alkoxycarbonylalkyl, carboxyl, alkoxy, haloalkoxy, aralkoxy, cycloalkylalkoxy, alkylthio, aralkylthio, cycloalkylalkylthio, alkoxyalkyl, aralkoxyalkyl, alkylthioalkyl, aralkylthioalkyl, alkylaminoalkyl, aryloxyalkyl, arylthioalkyl, hydroxyl, amino, hydroxyalkyl, haloalkyl, cycloalkyl, cycloalkylalkyl, aralkyl, halo, alkylamino, aralkylamino, N-alkyl-N-aralkylamino, N-alkyl-N-cycloalkylalkylamino, arylcarbonyloxyalkyl, arylcarbonylthio, alkoxycarbonyloxyalkyl, alkylaminocarbonyloxyalkyl, alkoxycarbonylthioalkyl and alkylaminocarbonylthioalkyl;

R⁶ is selected from cycloalkyl, cycloalkenyl and aryl; wherein R⁶ is optionally substituted at a substitutable position with one or more radicals independently selected from alkyl, cyano, carboxyl, alkoxycarbonyl, haloalkyl, hydroxyl, hydroxyalkyl, haloalkoxy, amino, alkylamino, arylamino, aminoalkyl, nitro, alkoxyalkyl, alkylsulfinyl, alkylsulfonyl, aminosulfonyl, halo, alkoxy and alkylthio; and R⁷ is selected from lower alkyl, hydroxyl and amino;

a prodrug thereof or a pharmaceutically acceptable salt of said selective COX-2 inhibitor of formula II or said prodrug.

12. A method of claim 11 wherein said ARI is fidarestat, epalrestat, minalrestat, SPR-210, zenarastat or zopolrestat, a prodrug thereof or a pharmaceutically acceptable salt thereof or of said prodrug.

13. A method of claim 11 wherein said ARI is zopolorestat, a prodrug thereof or a pharmaceutically acceptable salt of zopolrestat or said prodrug.

14. A method of claim 11 wherein said COX-2 inhibitor is valdecoxib, a prodrug thereof or a pharmaceutically acceptable salt of valdecoxib or said prodrug.

15. A method of claim 12 wherein said COX-2 inhibitor is valdecoxib, a prodrug thereof or a pharmaceutically acceptable salt of valdecoxib or said prodrug.

16. A method of claim 13 wherein said COX-2 inhibitor is valdecoxib, a prodrug thereof or a pharmaceutically acceptable salt of valdecoxib or said prodrug.

\* \* \* \* \*